US011642221B2

(12) United States Patent
Doran et al.

(10) Patent No.: US 11,642,221 B2
(45) Date of Patent: May 9, 2023

(54) IMPLANTABLE DEVICE HAVING ROUNDED STRUTS AND METHOD OF MANUFACTURE

(71) Applicant: Boston Scientific Scimed, Inc., Maple Grove, MN (US)

(72) Inventors: Burns Doran, Monticello, MN (US); Kelsey Cooper, Andover, MN (US); Graham Krumpelmann, Stillwater, MN (US); Ted Pelzer, Otsego, MN (US); Joshua Mark Inouye, Maple Grove, MN (US); Mark McPhail, Maple Grove, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 0 days.

(21) Appl. No.: 17/125,186

(22) Filed: Dec. 17, 2020

(65) Prior Publication Data

US 2021/0228355 A1 Jul. 29, 2021

Related U.S. Application Data

(60) Provisional application No. 62/966,805, filed on Jan. 28, 2020.

(51) Int. Cl.
*A61F 2/24* (2006.01)
*A61F 2/848* (2013.01)

(52) U.S. Cl.
CPC .......... *A61F 2/2445* (2013.01); *A61F 2/2442* (2013.01); *A61F 2002/8483* (2013.01);
(Continued)

(58) Field of Classification Search
CPC .......................................... A61F 2/2442–2445
See application file for complete search history.

(56) References Cited

U.S. PATENT DOCUMENTS 9,622,862 B2   4/2017 Lashinski et al.
2007/0250161 A1   10/2007 Dolan
(Continued)

OTHER PUBLICATIONS

International Search Report and Written Opinion for the International Patent Application No. PCT/US2020/065582, dated May 17, 2021, 18 pages.

*Primary Examiner* — Rebecca S Preston
(74) *Attorney, Agent, or Firm* — Seager, Tufte & Wickhem LLP

(57) ABSTRACT

An implant includes a frame comprising a tubular body formed by a plurality of interconnected struts that are manufactured to reduce stresses and strains resulting from component interaction during chronic use. At least a portion of a longitudinal corner of one or more struts of the frame may be chamfered, rounded, or otherwise modified to distribute stresses experienced at the strut corner throughout the strut body. Chamfering and/or rounding corners along at least a portion of a strut of the frame may reduce stresses on the frame caused by interactions between the frame and other components of the implant. The implant may be manufactured by cutting (e.g., laser cutting) a plurality of struts from a tubular metal alloy, polymer, or the like forming the tubular body, and softening at least a portion of an edge of the strut by cutting, grinding, and/or microblasting the edges of the corner.

19 Claims, 9 Drawing Sheets

(52) U.S. Cl.
CPC .......... *A61F 2220/0016* (2013.01); *A61F 2220/0041* (2013.01); *A61F 2230/0006* (2013.01); *A61F 2230/0008* (2013.01); *A61F 2230/0034* (2013.01); *A61F 2240/00* (2013.01); *A61F 2250/001* (2013.01); *A61F 2250/0039* (2013.01)

(56) References Cited

U.S. PATENT DOCUMENTS

| | | |
|---|---|---|
| 2012/0010701 A1* | 1/2012 | Bulman-Fleming .......... A61F 2/2445 623/2.37 |
| 2014/0236292 A1 | 8/2014 | Braido |
| 2017/0135816 A1 | 5/2017 | Lashinski et al. |
| 2018/0228610 A1 | 8/2018 | Lashinski et al. |

* cited by examiner

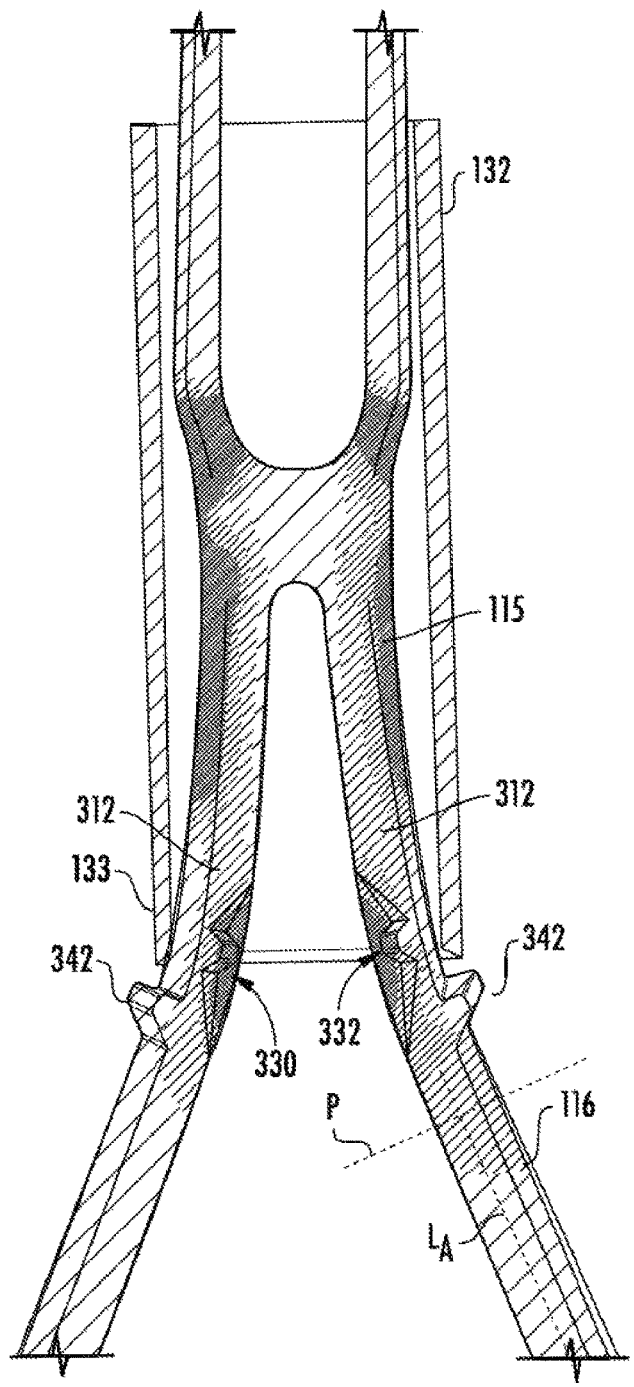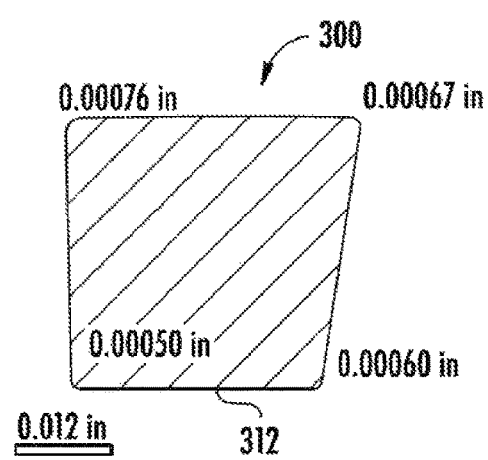
FIG. 3A
PRIOR ART
FIG. 3B
PRIOR ART

IMPLANTABLE DEVICE HAVING ROUNDED STRUTS AND METHOD OF MANUFACTURE

CROSS-REFERENCE TO RELATED APPLICATIONS

The present application claims the benefit of priority under 35 U.S.C. § 119 to U.S. Provisional Patent Application 62/966,805, filed Jan. 28, 2020, which application is incorporated herein by reference in its entirety for all purposes.

FIELD

The present disclosure relates generally to the field of implantable medical devices. In particular, the present disclosure relates to medical devices, systems, and methods for cardiac treatment.

BACKGROUND

Mitral regurgitation occurs when the native mitral valve fails to close properly, causing blood to flow back into the left atrium from the left ventricle during the systolic phase of heart contraction.

Annuloplasty is performed to regain mitral valve competence by restoring the physiological form and function of the normal mitral valve. Annuloplasty procedures may involve implanting a structure, such as a ring, stent, frame or the like within the heart. Cardiac implants are subject to the chronic stresses and strains associated with cardiac muscle palpitation and it would thus be desirable to reduce the impact of chronic forces on a cardiac implant.

SUMMARY

According to one aspect, an implant for reshaping a valve annulus includes a tubular frame including an elongate strut including a proximal portion, a distal portion, and a plurality of sides, wherein adjacent sides extend or are joined along a respective strut edge or corner, and where the proximal portion includes a rounded portion extending at least partially along the proximal portion of the elongate strut and including a rounded corner.

In various embodiments, the rounded portion may include at least two corners each rounded to a common corner radius. The rounded portion may include at least two corners each having different corner radius. The rounded portion may have one of a semicircular, ovoid, or circular cross section. In one embodiment, the rounded portion of a pair of adjacent elongate struts may be oriented towards each other. In various embodiments, the rounded corner may include a corner radius of at least about 0.001" and at most about 0.1".

In some embodiments, the implant may further include a collar disposed at least partially around a proximal apex of a pair of adjacent elongate struts, the collar including a proximal end and a distal end and disposed to axially translate along the pair of adjacent elongate struts to a distal extent of travel, where each elongate strut of the pair of adjacent elongate struts may include at least one rounded portion disposed at least partially within the distal end of the collar at the distal extent of travel of the collar. The implant may include a shaft carried by the proximal apex of the pair of adjacent elongate struts and having an outer thread, the shaft configured to rotate about a rotation axis. The collar may have an inner thread engaged with the outer thread of the shaft and rotation of the shaft about the rotation axis may cause the collar to axially translate along the pair of adjacent elongate struts to change an angle between the pair of adjacent elongate struts.

In one embodiment, the elongate strut may be one of a plurality of elongate struts of the tubular frame, and the plurality of elongate struts may be joined in pairs at their proximal portions to provide a plurality of pairs of adjacent elongate struts. The plurality of pairs of adjacent elongate struts may also be joined at their distal portions to provide a plurality of distal apices, and the implant may include a plurality of anchors translatably supported by the plurality of distal apices.

According to another embodiment, an implant includes a frame including a plurality of elongate struts, at least two elongate struts including a proximal portion, a distal portion, and a plurality of sides wherein adjacent sides extend or are joined along a respective strut edge or corner, and where the proximal portion includes a rounded portion extending at least partially along the proximal portion of the elongate strut and including a rounded corner. The implant may further include a plurality of anchors. The proximal portion of the elongate strut is joined to an adjacent elongate strut to form a pair of adjacent elongate struts having a proximal apex, and where the pair of adjacent elongate struts is joined to an adjacent pair of elongate struts at a distal apex, the distal apex configured to support an anchor. A collar is disposed at least partially around the proximal apex of the pair of adjacent elongate struts, the collar including a proximal end and a distal end, the collar configured to axially translate along the pair of adjacent elongate struts to a distal extent of travel, where the rounded portions of the elongate struts of the pair of adjacent elongate struts are at least partially within the distal end of the collar in the distal extent of travel of the collar.

In various embodiments, the rounded portion may include at least two corners each rounded to a common corner radius or a different corner radius. The rounded portion may have one of a semicircular, ovoid, or circular cross section. In some embodiments, the rounded portion of a pair of adjacent elongate struts are oriented towards each other. The rounded corner may include a corner radius at least about 0.001" and at most about 0.1". In some embodiments, at least two elongate struts each include one or more rounded corners, and a degree of rounding of the one or more rounded corners of each of the at least two elongate struts may differ.

According to a further aspect, a method of manufacturing an implant including a tubular frame is provided, wherein the tubular frame includes an elongate strut including a proximal portion, a distal portion, and a plurality of sides wherein adjacent sides extend or are joined along a respective strut edges or corner, and where the proximal portion includes a rounded portion extending at least partially along the proximal portion of the elongate strut and including a rounded corner. The method includes cutting the elongate strut from a metal tube and performing a rounding process on the elongate strut to form the rounded corner, the rounding process including cutting (e.g., laser cutting), grinding, milling, electropolishing, micro-blasting, etching, or a combination thereof.

In various embodiments, the method may include everting the tubular frame, or masking the tubular frame, or both. The rounded corner may be associated with a first edge or corner of the elongate strut and may include a first corner radius, and the rounding process may include performing the rounding process on a second edge or corner of the elongate strut to provide a second rounded corner having a second corner radius that is common or different from the first corner radius. In one embodiment, performing the rounding process on the second corner occurs simultaneously with performing the rounding process on the first corner. In one embodiment, the elongate strut is one of a plurality of elongate struts of the tubular frame, and the method includes performing the rounding process on each of the plurality of elongate struts of the tubular frame, where at least two rounded portions of at least two different elongate struts are similar or different.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

FIG. 3A illustrates a cross section view of a portion of a prior art implant provided to illustrate stress imparted upon struts by the collar of the implant and resulting strain;

FIG. 3B illustrates a cross section view of a strut of the prior art implant of FIG. 3B;

DETAILED DESCRIPTION

Figure 1:
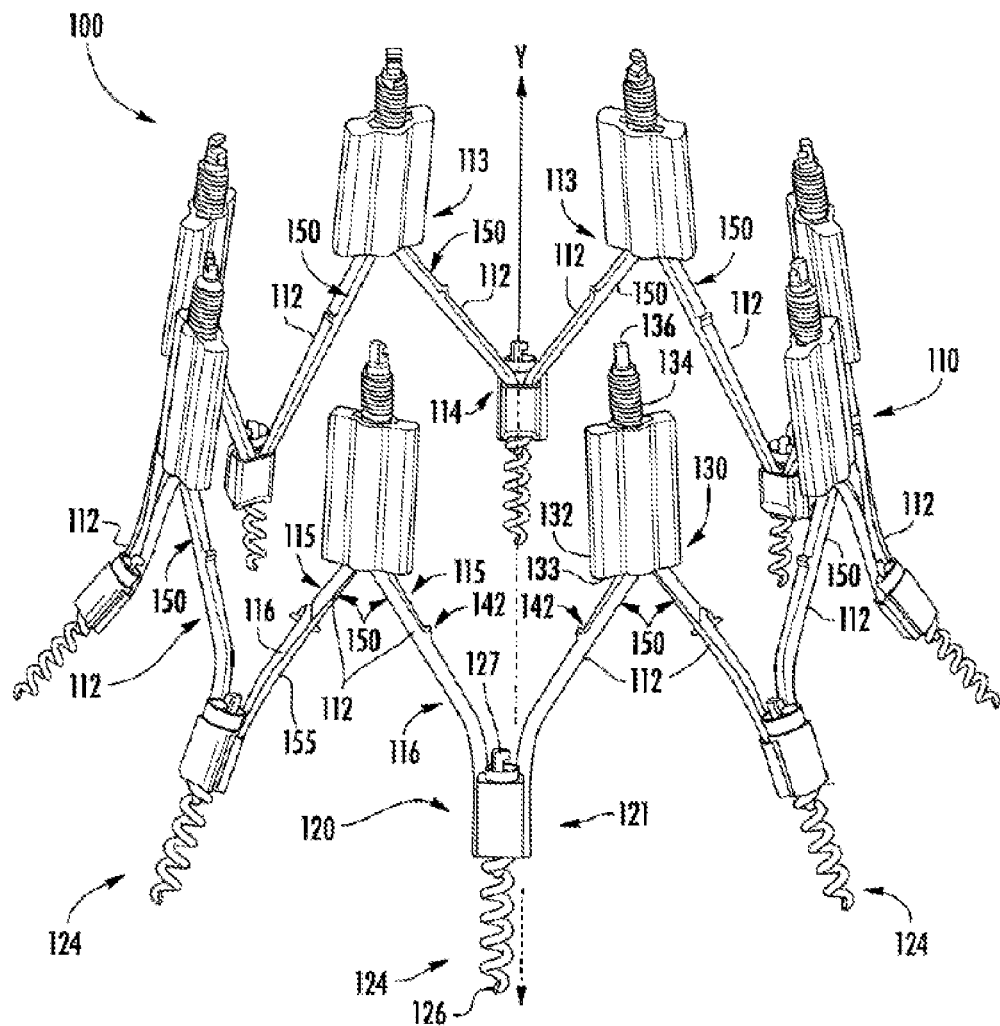
FIG. 1 illustrates one embodiment of a resilient implant manufactured as disclosed herein.

An implant as disclosed herein includes a frame comprising a tubular body formed by a plurality of elongate struts that are manufactured to increase strut resiliency by distributing strain along the strut, the strain resulting from component interaction during chronic use. In one embodiment, each elongate strut comprises a proximal portion, a distal portion, and a plurality of sides, adjacent sides extending or joined along a respective strut edge or corner (hereinafter "corner" for the sake of convenience without intent to limit). At least a predetermined portion of the elongate strut may be modified to increase a corner radius or otherwise round off one or more strut corners of the predetermined portion to more effectively distribute strains caused by stresses related to interaction of implant components due to the chronic palpatory motion of the heart, wherein the corner radius is known in the art to refer to the radius of a circle created by extending the corner arc to form a complete circle.

Corner rounding one or more strut corners may be one aspect of a manufacturing process of the implant frame. For example, the implant may be manufactured by cutting (e.g., laser cutting) a plurality of struts from a tube, to form the tubular body, and applying the rounding process to various corner locations on the strut which experience stress and/or strain during use. The corner rounding process may include chamfering, grinding, milling, etching, or micro-blasting predetermined portions of the frame to increase the corner radius for those predetermined portions of the frame. In some embodiments, accessibility of the predetermined portions may be enhanced by everting the frame during the manufacturing process to more easily expose the corners to rounding tools. Such a manufacturing process provides an implant with improved resiliency in the presence of chronic palpatory forces.

Various embodiments of such an implant and method of manufacture will now be described. Reference in this specification to "one embodiment," "an embodiment," or "in some embodiments" means that a particular feature, structure, or characteristic described in connection with the embodiment is included in at least one embodiment of the invention. The appearances of the phrases "one embodiment," "an embodiment," or "in some embodiments" in various places in the specification are not necessarily all referring to the same embodiment, nor are separate or alternative embodiments necessarily mutually exclusive of other embodiments. Moreover, various features are described which may be exhibited by some embodiments and not by others. Similarly, various requirements are described which may be requirements for some embodiments but may not be requirements for other embodiments.

As used herein, the term "distal" refers to the end farthest away from the medical professional when introducing a medical device into a patient, while the term "proximal" refers to the end closest to the medical professional when introducing a medical device into a patient. A central axis means, with respect to an opening, a line that bisects a center point of the opening, extending longitudinally along the length of the opening when the opening comprises, for example, a tubular frame, a strut, or a bore.

Although embodiments of the present disclosure may be described with specific reference to an implant for use with mitral valves, it is appreciated that various other implants may similarly benefit from the structures and manufacturing methods disclosed herein. For example, implants which must withstand the palpatory forces for repairing a tricuspid valve annulus and/or addressing other dilatation, valve incompetency, valve leakage and other similar heart failure conditions may also benefit from the concepts disclosed herein.

FIG. 1 illustrates an implant 100 comprising a frame 110 that may be disposed about a heart valve or other cardiac feature. In one embodiment, the frame 110 may extend circumferentially around and partially axially along a central frame axis Y extending proximally-distally through a center point of the frame. The terms "inner," "inward," and the like refer to directions generally toward the axis Y, and terms "outer," "outward," and the like refer to directions generally away from the axis Y. These geometric references generally apply unless otherwise indicated, either explicitly or by context.

The frame 110 may form a generally tubular shape, where herein "tubular" includes circular, rounded, ellipsoidal, segmented, or other shapes or combination thereof, as well as other rounded or otherwise closed shapes. The frame 110 may be configured to change shape, size, and/or configuration. For example, the frame 110 may assume various shapes, sizes, configurations etc. during different phases of deployment such as during pre-delivery, delivery, tissue engagement, and cinching. In one embodiment, in an unconstrained state, for example, at delivery, the frame 110 may have an overall axial height in the range of 15 millimeters (mm) to 20 mm, although the present disclosure is not so limited.

According to one embodiment, the frame 110 may be formed from one or more struts 112 that may form all or part of the frame 110, where at least one the struts 112 may include elongated structural members formed of a metal alloy, a shape memory material, such as an alloy of nickel titanium or other metals, metal alloys, plastics, polymers, composites, other suitable materials, or combinations thereof. In FIG. 1 sixteen struts 112 are shown although it is appreciated that in some embodiments, there may be fewer or more than sixteen struts. In some embodiments, there may be at least two, four, six, eight, ten, twelve, fourteen, eighteen, twenty, twenty-two, twenty-four, twenty-six, twenty-eight, thirty, or more struts 112.

In some embodiments, one or more of the struts 112 may be formed from the same, monolithic piece of material (e.g., tube stock). Thus, the struts 112 may refer to different portions of the same, extensive component. In other embodiments, one or more of the struts 112 may be formed separately and attached permanently together, e.g., by welding, etc. In some embodiments, the struts 112 may be separate components that are detachably coupled together by other components of the implant 100. For example, the struts 112 may be held together via various components described herein, such as collars 132, anchoring assemblies 120, other features, or combinations thereof. In some embodiments, separate strut units may include two or more struts permanently attached together such as at an apex, and the separate units may each be coupled together, either permanently or detachably, to form the frame 110. In some embodiments, the struts 112 may be attached by hinges, pins, or other suitable means.

In one embodiment, at least one of the struts comprises a proximal portion 115 (not fully visible in FIG. 1) comprising a rounded portion 150, and a distal portion 116. According to one aspect, the at least one strut 112 comprises a plurality of sides extending or joined along a plurality of respective edges corners, and is generally trapezoidal in cross-section, wherein a shape of at least one corner (such as corner 155) is modified (e.g., chamfered, rounded, or otherwise modified to reduce a sharpness of the corner) in the rounded portion 150 of the proximal portion 115 to modify the corner radius of at least one corner to distribute strain resulting from interaction with the collar 132 along the strut 112. The struts may vary in width and thickness along their longitudinal axis to allow for different beam characteristics and forces applied as the collars 132 are distally translated over the struts 112, for example for post implantation constriction or remodeling of a valve annulus. For the sake of convenience, without intent to limit, reference will be made generally to the "struts" although the descriptions need not apply to all struts of a given frame.

In one embodiment, the relatively longer sides of the trapezoidal cross-section of the struts 112 extend along the circumference of the frame 110. "Circumference" as used herein generally refers to a perimeter or boundary and can refer to a circular or other rounded or non-rounded path lying in a plane substantially transverse to the axis, unless otherwise stated. The short ends of the rectangular cross-section of the struts 112 extend transversely to the circumference of the frame 110. In some embodiments, other configurations and/or cross-sectional shapes of the struts 112 may be implemented.

The struts 112 extend around the axis to form the various shapes of the frame 110. The struts 112 are arranged such that the wall pattern of the frame 10 may be approximately sinusoidally or zig-zag shaped. In some embodiments, the wall pattern may have other suitable shapes, sinusoidal or otherwise. The vertices of the sinusoidal shaped frame 110 may be pointed or rounded.

In one embodiment, pairs of adjacent struts 112 meet at an apex. At least a first pair of adjacent struts 112 meets at a proximal apex 113 at a proximal portion of the implant 100 and at least a second pair of adjacent struts 112 meets at a distal apex 114 at a distal portion of implant 100. In one embodiment, the proximal and distal apices 113, 114 are spaced sequentially along the circumference of the frame 110, with a proximal apex 113 followed by a distal apex 114, followed by a proximal apex 113, etc. In the illustrated embodiment, there are eight proximal apices 113 and eight distal apices 114, although the disclosure is not so limited, and embodiments are envisioned where there may be no more than about six or four or fewer or more than eight or ten or twelve proximal and distal apices 113, 114 depending on the number of struts 112.

In one embodiment, the proximal apices 113 are each configured to support a restraint such as an actuator 130 fitted over and/or around the upper apex 113. In one embodiment, the actuator 130 includes an actuator shaft 134 that is rotatably carried by the proximal end of the frame 110, for example, a head of the actuator shaft 134 may be carried by a window or other opening (not shown) at the proximal apex of the frame 110. The actuator shaft 134 may include a drive coupler 136 at the proximal end. The actuator 130 may further include an actuator collar 132 having internal features configured to interact with the features of the actuator shaft 134 such that rotation of the actuator shaft 134 by an actuator drive tube coupled to the drive coupler 136 axially translates the actuator collar 132 over the actuator shaft 134 and over struts 112. In some embodiments, "axial" as applied to axial movement or restraint of the actuator collar includes directions that are at least partially in the proximal or distal direction and that are parallel or generally parallel to a central axis extending through (proximally—distally) the frame, such as at least partially in or along axis Y. As shown in FIG. 1, struts 112 extend away from the proximal apex in opposing directions. Distal advancement of the actuator collar 132 over struts 112 pulls the struts together within the actuator collar 132, thereby 'cinching' the frame and reducing the distance between anchoring assemblies 120 to reshape heart tissue anatomy, for example to restore a valve to its native configuration. In one embodiment, each actuator collar 132 may be independently actuated in accordance with the reshaping objective for the associated anchor pair. In one embodiment, each strut 112 may include a feature, such as nub 142, to limit an extent of distal travel of the actuator 130 along the struts.

According to one embodiment, the collar 132 of the actuator 130 thus may be distally translated over the struts 112 until a distal end of the collar contacts the nub 142, inhibiting further distal translation. As the collar 132 advances distally, cinching the struts 112, a distal end 133 of the collar applies force to the struts 112 to enable cinching. As will be describe later herein, chronic stress between the distal end 133 of the collar and the struts 112 may strain the strut 112. In one embodiment, the strut 112 may be advantageously manufactured such that predetermined portions of the struts, such as portion 150 of the proximal portion 115 which contacts the distal end 133 of the collar 132 (and over which the collar 132 is translated), are rounded or otherwise configured to modify a corner radius to distribute or otherwise divert strains experienced by the struts in the presence of chronic stress throughout the strut 112.

In one embodiment, distal apices 114 of the implant 100 support a plurality of anchoring assemblies 120, the anchoring assemblies including anchor housings 121 and anchors 124. In one embodiment, anchors 124, comprising a helical coil 126 and a coupler 127 may be translatably disposed within anchor housings 121. The coupler 127 may be rotatably coupled to a drive tube (not shown) that rotatably advances the anchor 124 through the anchor housing 121 into tissue, such as into tissue of a valve annulus. In various embodiments, at least two and optimally at least four or six or all of the distal apices 114 include anchor housings 121.

In some embodiments, the anchors 124 may be made of a suitable biocompatible metal alloy such as stainless steel, cobalt chromium, platinum iridium, nickel titanium, other suitable materials, or combinations thereof. Each anchor 124 may be sharpened at its distal point, or leading turn, so as to facilitate penetration into the cardiac tissue. Each anchor 124 may be at least about 10 mm and/or at most about 15 mm in total axial length. In some embodiments, the anchors 124 may be shorter or longer than 10 mm to about 15 mm in total axial length. By "total" axial length it is meant the axial length of the anchor 124 from the end of the distal penetrating tip of the helical coil 126 to the opposite, proximal end of the coupler 127. The helical coil 126 may be at least about 6 mm and/or at most about 12 mm in axial length, i.e., in an axial direction. In some embodiments, the helical portion of the anchor 124 may be shorter or longer than 6 mm to 12 mm in axial length.

Figure 2:
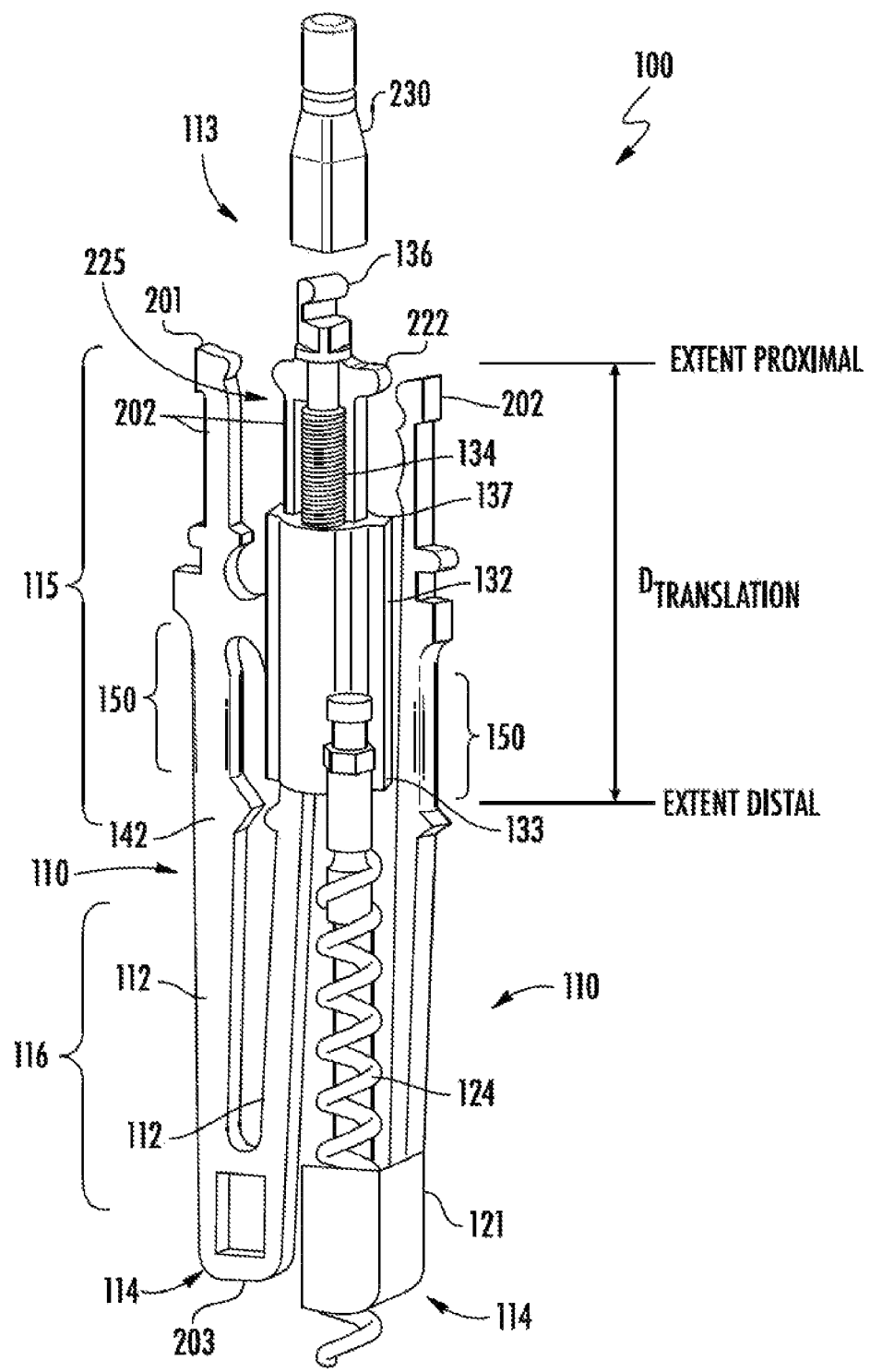
FIG. 2 illustrates a portion of the implant of FIG. 1 including a corner rounded portion manufactured as disclosed herein to distribute strain throughout the implant.

FIG. 2 illustrates one portion of the implant 100 and frame 110 including a plurality of struts 112, wherein the proximal portion 115 of strut 112, including the rounded portion 150, and distal portion 116 of strut 112 are shown in more detail. Proximal portion 115 of strut 112 extends from a proximal tip 201 of the strut 112 to the nub 142. Distal portion 116 of the strut extends from nub 142 to a distal end 203 of the strut 112. In the embodiment of FIG. 2, the distal ends of struts 112 are shown to be integrally joined, although the present disclosure is not so limited, and embodiments wherein the distal ends of the struts are separate, and joined, for example, by the anchor housing 121 or by the anchor 124 are considered to be equivalents.

In one embodiment, as illustrated in FIG. 2, arms 202 of adjacent struts are configured to cooperatively form a window 225 at the proximal apex 113, wherein the shaft 134 may be disposed for free rotation within the window 225. In one embodiment, the collar 132 acts to retain the shaft 134 within the window 225 formed by the arms 202 of struts 112. Rotation of a driver 230, which may be coupled to coupler 136 and actuated by a drive tube (not shown), may rotate the shaft 134 within the window 225, causing cooperating threads in an internal bore of the collar 132 to interact with threads of the shaft 134 to axially translate the collar 132 along the proximal portion 115 of the struts 112, including along the rounded portion 150. In one embodiment, the translation distance traveled by the collar 132, indicated as $D_{TRANSLATION}$ in FIG. 2, is from Extent $_{PROXIMAL}$ wherein translation of a proximal end 137 of the collar 132 is limited by flanges 222 of arms 202, and Extent $_{DISTAL}$, wherein further distal travel of the distal end 133 of the collar 132 is inhibited by the nub 142. In FIG. 2, an anchor 124 is shown proximally disposed in anchor housing 121, a configuration that is associated with a compressed, delivery configuration of the frame 110, wherein distal apices and proximal apices may be compressed together within a delivery catheter.

Following delivery, the frame 110 may be expanded, increasing distances among the proximal apices 113 and distal apices 114 to enable the frame to surround or partially surround a valve annulus. Expanding distances between the distal apices 114 increases stress applied by the distal end 133 of the collar 132 on the strut 112, straining the struts 112.

For example, FIGS. 3A and 3B illustrate various views of a prior art strut 312. FIG. 3B is a cross sectional view 300 of strut 312 taken along an axis P perpendicular to a longitudinal axis LA of the strut 312 and shows the strut to be generally trapezoidal in cross section with corner radii in the range of about 0.00050 in=0.00076 in (0.0127 mm–0.0193 mm). It will be appreciated that the strut 312 illustrated in FIG. 3A has not been subjected to any specific rounding operations (such as disclosed herein), only typical operations that are currently used (e.g., microblasting and electropolishing). The rounding operations disclosed herein would tend to increase these "nominal" radii by up to about half of the strut width, the widths generally being at least about 0.25 mm and at most about 1.5 mm. FIG. 3A is a strain map illustration of a portion of the strut 312, wherein darker portions of the illustration indicate a larger amount of strain being experienced at the corresponding location of the strut 312. In FIG. 3A, the collar 132 is shown in cross-section to enable viewing of the impact of stress, imparted by the collar 132, and resulting strain realized by the strut 312.

In FIG. 3A, the collar 132 has been distally advanced over the strut to a distalmost extent, e.g., wherein further travel of the distal end 133 of the collar 132 is inhibited by contact of the collar 132 with nubs 342 of the struts 312. As shown in FIG. 3A, the stress of the collar 132 on the strut 312 results in high areas of strain in portions 330, 332 of the strut 312.

According to one aspect, it is realized that modifying the corner radius of at least one corner of the strut acts to distribute the strains experienced by the strut along a larger surface area of the strut, thereby increasing the resiliency of the strut to the stress of chronic use.

Figure 4A:
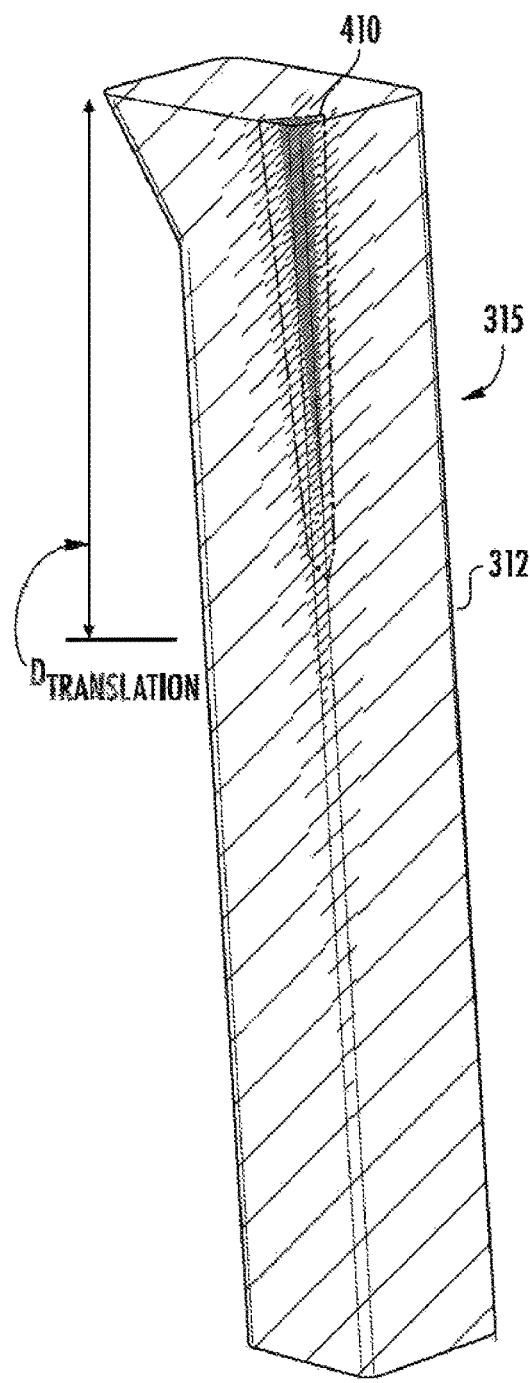
FIGS. 4A and 4B illustrate strain maps of a prior art strut and a strut manufactured as disclosed in one embodiment.

For example, FIG. 4A is a strain map of the strut 312 of FIGS. 3A and 3B, wherein darker areas of the strut correspond to higher levels of strain experienced by the strut. As shown in FIG. 4A, the strut 312 experiences high levels of strain over the proximal end 315 of the strut, particularly in the area 410 which relates to the translation distance $D_{TRANSLATION}$ of the collar (not shown).

Figure 4B:
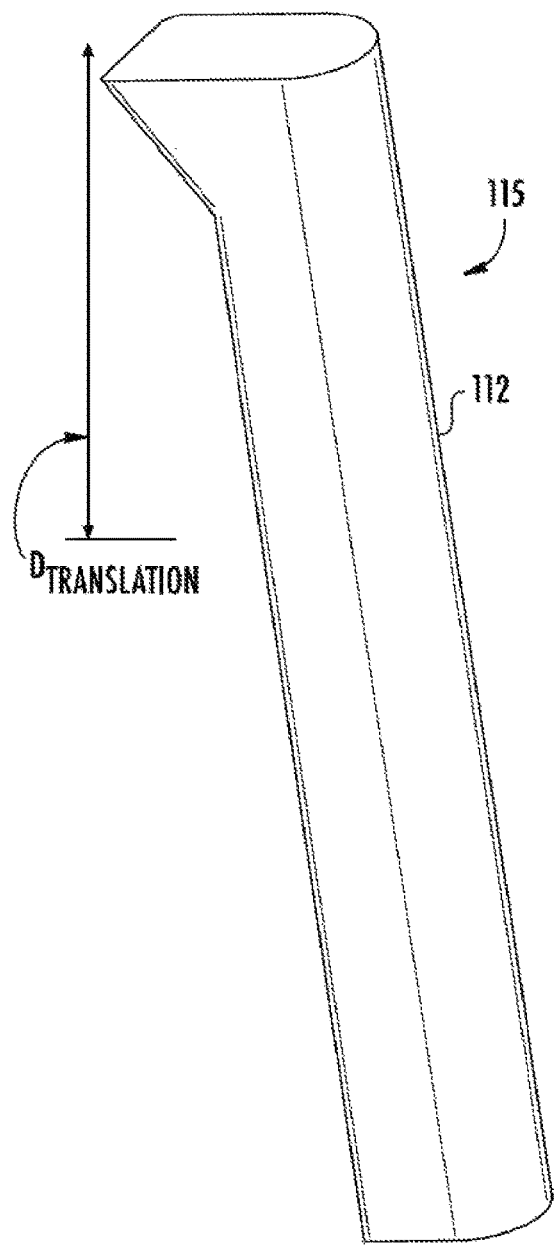

In contrast, FIG. 4B has been manufactured using a processing method that increases the corner radius of at least two corners of the proximal portion 115 of strut 112 (the corners or edges along which sides of the strut 112 extend or are joined along), for example, forming the strut 112 into a half round configuration that distributes the strain along the body of the strut 112. As a result, stresses resulting from travel of a collar along the translation distance $D_{TRANSLATION}$ of the strut 112 are more effectively distributed along the strut body, thereby protecting the strut 112 from adverse effects of chronic stress, such as fracture.

It is thus appreciated that manufacturing the implant to reduce the corner radius of one or more edges of the strut (in any of a variety of combinations of edges) may improve the resiliency of the strut. In an embodiment of an implant manufactured as disclosed herein, wherein the strut is generally trapezoidal in cross-section, it is appreciated that resiliency can be improved by modifying the corner radius for one or both of the corners of a strut that define a strut surface oriented towards the other strut within the collar, e.g., the surface that opposes the surface of the strut experiencing cinching force from the collar. Alternatively, or in conjunction, in some embodiments resiliency may be improved by modifying one or both of the strut corners that define a strut surface facing any of the interior walls of the collar (facing central frame axis Y shown in FIG. 1). Alternatively, in some embodiments, resiliency may be improved by modifying the corner radius of all of the corners of the strut. In some embodiments, a degree of corner radius modification may be common for two or more corners that are modified. In some embodiments, a degree of corner modification may differ for at least two corners that have a modified corner radius.

Figure 5:
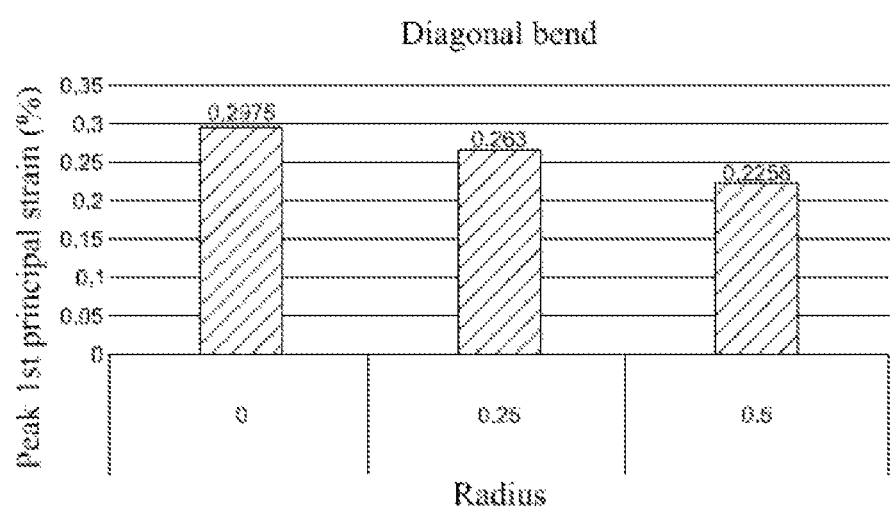
FIG. 5 illustrates examples of strain reductions for varying corner radii of a strut.

Although in various embodiments the corner radii may be modified to be at least, for example, about 0.001" (0.0254 mm) and at most, for example, about 0.1" (0.254 mm), the present disclosure is not limited to any particular amount or degree of corner radius modification. FIG. 5 illustrates strain reduction achieved for varying a corner radius of a strut from the prior art essentially sharp edge or corner (0 radius) to a radius of about 25% of the width of the strut (providing a half round strut), and to a radius of about 50% of the width of the strut (providing a circular strut). The illustrated strain reduction is generally in the region of the rounded corner or edge of the strut along which the sidewalls of the strut extend or are joined. It will be appreciated that the examples of FIG. 5 are with respect to a strut with a substantially square cross-section. The principles of rounding a strut corner in accordance with the present disclosure may be applied to struts of other cross-sections with walls joined or extending along corners or edges, such as non-square polygons (e.g., shapes with four or more sides extending or joined along corners or edges). In general, rounding within the scope of the present disclosure to achieve the desired strain reduction can include rounding to form a corner with a radius of at least about 10% of the width of the strut, such as at least about 25% of the width of the strut, such as at least about 50% of the width of the strut, or any incremental percentage therebetween. In one aspect, the width may be considered as the smallest dimension or average dimension across the cross-section.

Figure 6A:
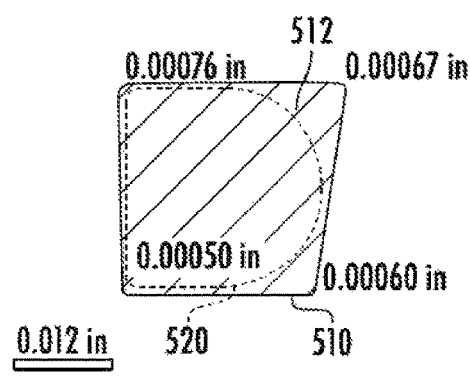
FIGS. 6A and 6B illustrate perspective views of one embodiment of a corner rounded strut and its use in a frame manufactured to dissipate stresses as disclosed herein.
Figure 6B:
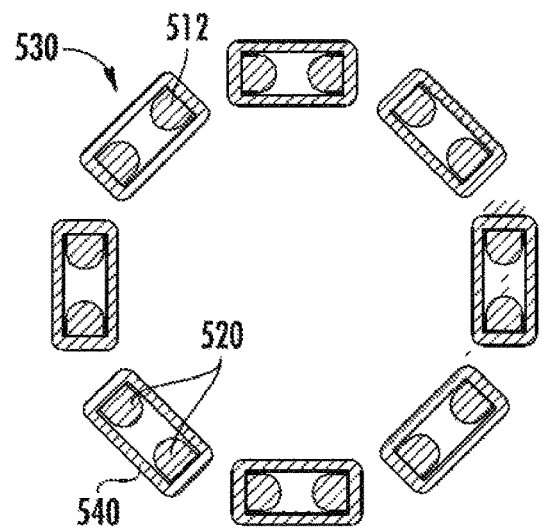

FIGS. 6A and 6B illustrate a cross section of an example of a strut 512 having an initial cross-sectional shape 510 and a half-circular, 'D' shape 520 (shown in dashed lines in FIG. 6A) achieved following a rounding process during manufacture of the implant. FIG. 6B illustrates a cross section of an implant 530 (such as similar to implant 100 of FIG. 1), taken along a plane substantially perpendicular to a longitudinal axis of the implant 530, and showing one embodiment of the orientation of the modified struts 520 within collars 540, wherein the struts are configured such that rounded sides of the strut are oriented towards each other within the collar, thereby distributing strain caused by stresses of the collar 540 on the struts 520.

Figure 7A:
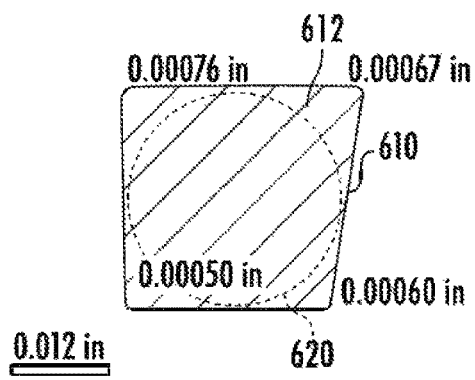
FIGS. 7A and 7B illustrate perspective views of one embodiment of a corner rounded strut and its use in a frame manufactured to dissipate stresses as disclosed herein
Figure 7B:
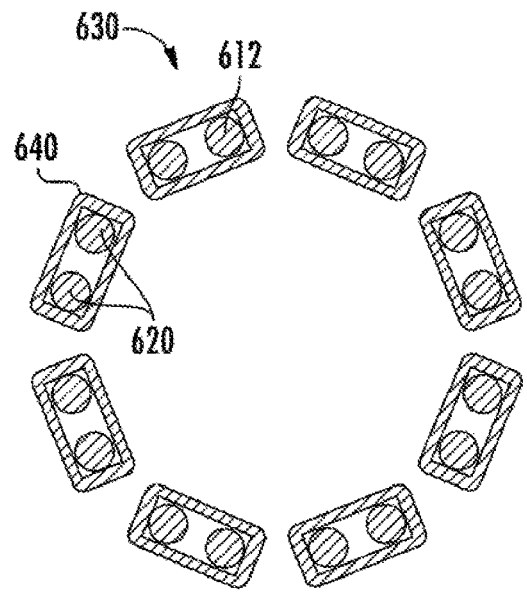

FIGS. 7A and 7B illustrate a cross section of an example of a strut 612 having an initial cross-sectional shape 610 and a circular, 'O' shape 620 (shown in dashed lines in FIG. 6A) achieved following a rounding process during manufacture of the implant. FIG. 7B illustrates a cross section of an implant 630, taken along a plane substantially perpendicular to a longitudinal axis of the implant 630, wherein the struts 620 are disposed in collars 640, and each strut has been modified to have rounded corners between strut surfaces.

It should be noted that although FIGS. 6B and 7B show struts each having a common cross section shape, the disclosure is not so limited. It is appreciated that there may be advantages to customizing the shape of struts in accordance with their anticipated position and corresponding palpatory forces following placement of the implant. Thus, embodiments wherein different corners of a strut have different corner radii, different struts of a frame have different numbers of corners that are rounded, and/or have corners rounded to different degrees, are considered to be within the scope of this disclosure.

Figure 8:
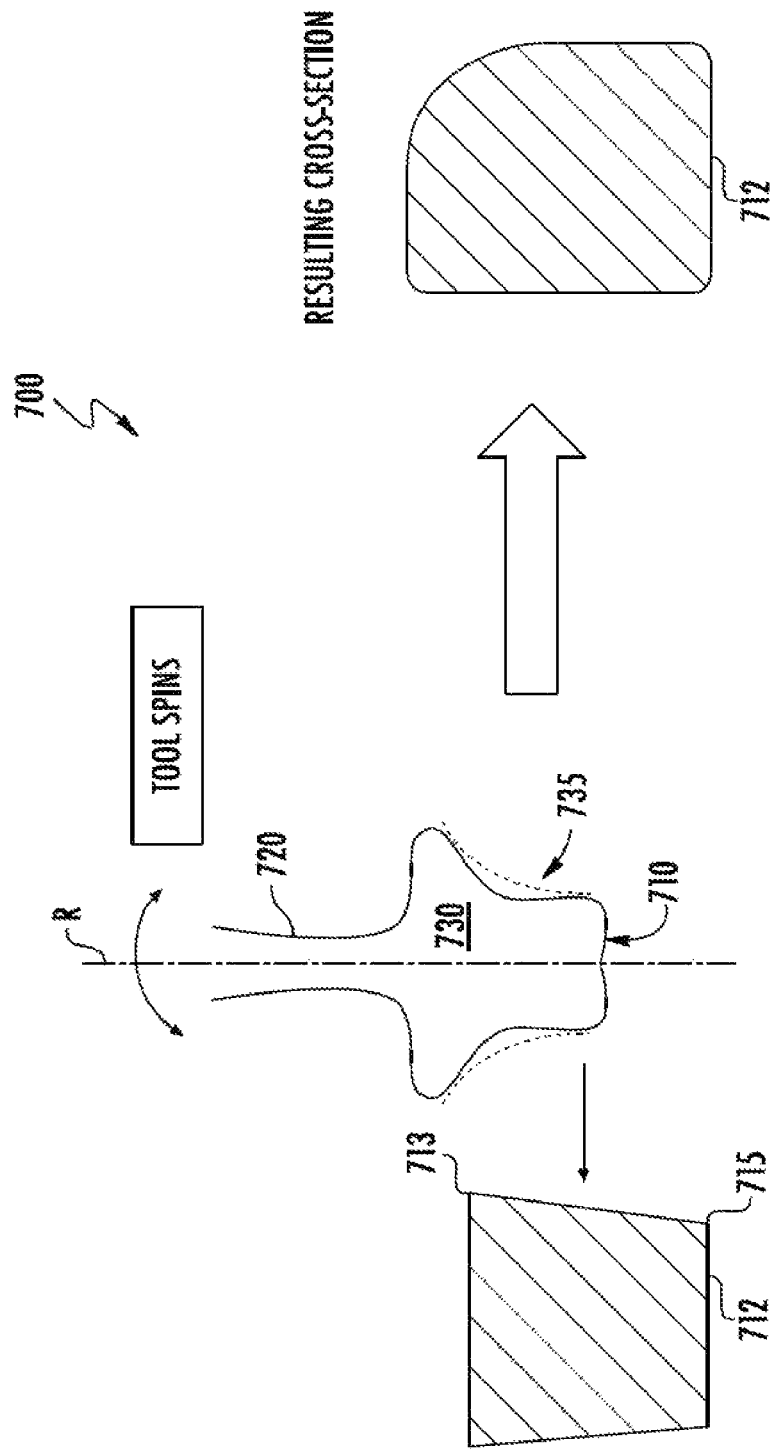
FIG. 8 illustrates one method of manufacture for embodiments of struts disclosed herein.

Referring now to FIG. 8, a system 700 for modifying at least one corner of a strut 712 of a frame is shown to include a mandrel 710, which may be rotatably disposed within a work table of a manufacturing facility. The mandrel 710 is shown to include a proximal neck portion 720 and a distal body 730 that diminishes in circumference along its distal longitudinal axis, forming a complementary curved portion 735 associated with a preselected corner radius. In one embodiment, the curved portion 735 may be coated with an abrasive material, such as diamond dust or other substance having a material hardness that exceeds a material hardness of the strut 712.

In one embodiment, a first corner of the strut 712 may be introduced to the mandrel 710 while the mandrel 710 is controlled to rotate about axis R to grind the strut 712 for corner rounding. The strut 712 is shown on the right in FIG. 8 following grinding of a first corner 713. In some embodiments, the strut may then be rotated to grind one or more other corners of strut 712, such as corner 715. In various embodiments, engagement of the strut 712 with the mandrel 710 may be controlled manually or via robotic assist.

In some embodiments, fine tuning of a corner radius may be performed using one or more milling bits. For example, in some systems, a strut may be reduced to a first corner 713 radius using a table mounted mandrel/grinding wheel, and the corner radii fine-tuned by hand or robotically using one or more milling bits to customize the strut.

Figure 9:
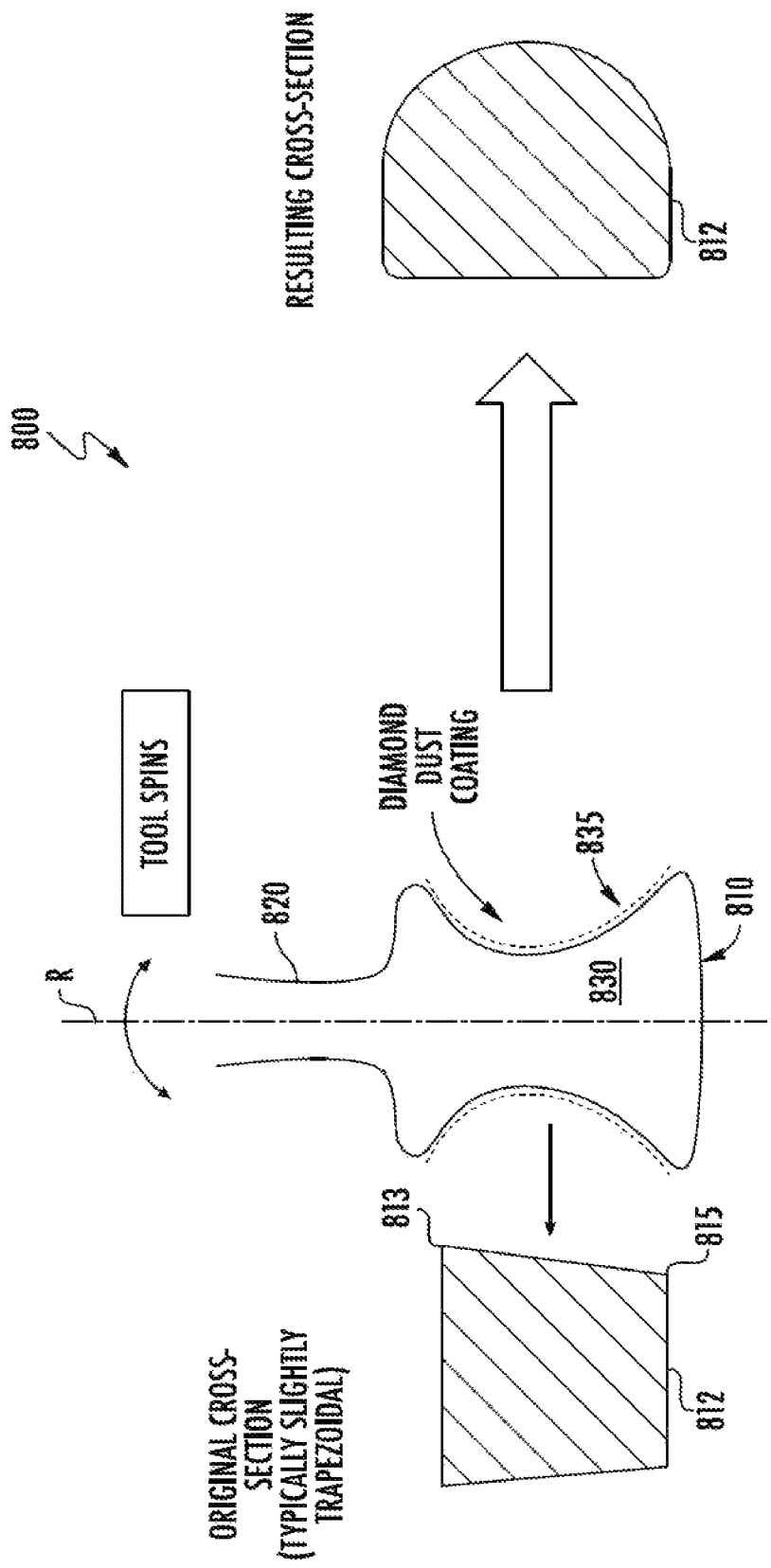
FIG. 9 illustrates one method of manufacture for embodiments of struts disclosed herein.

Referring now to FIG. 9, a system 800 for simultaneously modifying two corners of a strut 812 of a frame is shown to include a mandrel 810, which may be rotatably disposed within a work table of a manufacturing facility. The mandrel 810 is shown to include a proximal neck portion 820 and a distal body 830 that diminishes in circumference along its distal longitudinal axis to a center point of the body 830, then increases in circumference along the distal axis to about its original circumference, forming a concave portion 835 associated with a preselected strut curve. In one embodiment, the concave portion 835 may be coated with an abrasive material, such as diamond dust or other material having a material hardness that exceeds a material hardness of the strut 812.

In one embodiment, a first surface of the strut 812 may be introduced to the mandrel while the mandrel is controlled to rotate about axis R to grind the strut 812 for corner rounding. The strut 812 is shown on the right in FIG. 9 following grinding of the first surface, wherein the shapes of both corners 813, 815 of the strut 812 have been modified. In some embodiments, the strut may then be rotated to grind one or more other corners of strut 812. In various embodiments, engagement of the strut 812 with the mandrel 810 may be controlled manually or via robotic assist.

As discussed with regard to FIG. 8, in some embodiments, fine tuning of the corner rounding of the strut 812 may be performed using one or more milling bits. For example, in some systems, the mandrel 810 may be used to perform a rough modification of the curvature of the strut via a table mounted mandrel/grinding wheel, and the curve may be fine-tuned by hand or robotically using one or more milling bits.

In some embodiments, depending upon the location of a corner of the strut to be modified, the process of manufacturing the implant may include everting the frame one or more times (e.g., flipping the frame inside out) to improve line of sight and/or to facilitate exposure of strut corners to the shaping process.

Another method of manufacturing the implant may use a combination of laser cutting and micro-blasting. Micro-blasting is a process in which high pressure air and a fine powder are blended together in a chamber to form an abrasive mixture. The mixture may be directed at a high velocity through a nozzle onto the frame to deburr, finish, and/or further round the corner of the strut.

Figure 10:
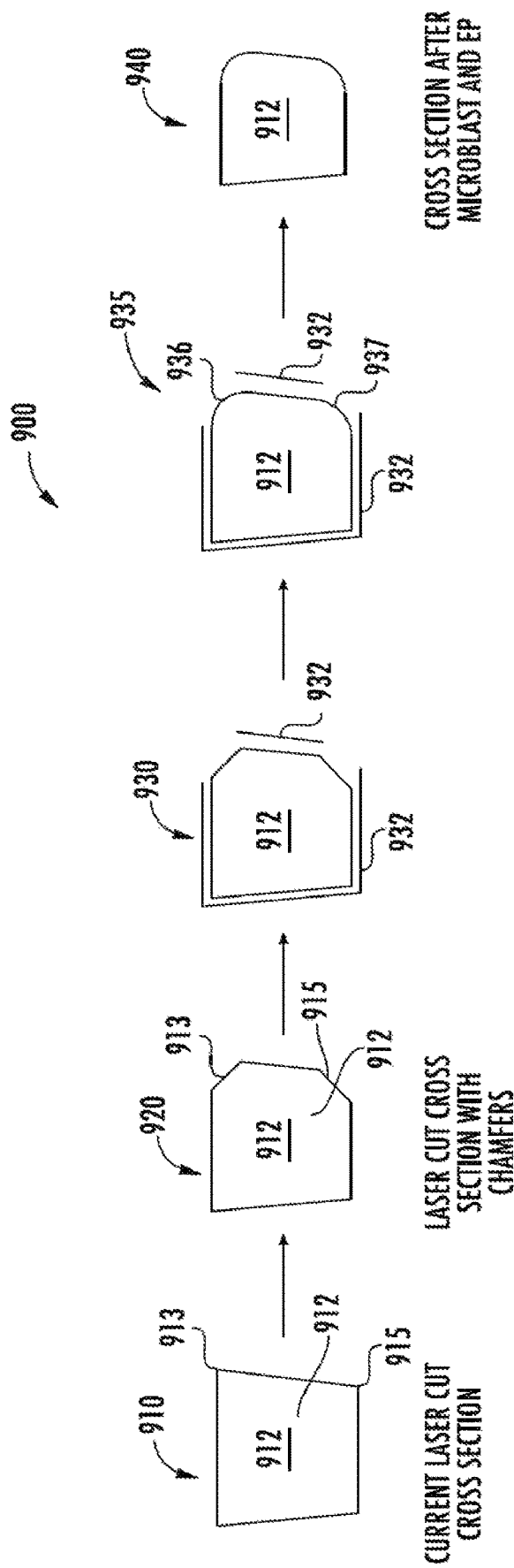
FIG. 10 illustrates one method of manufacture for embodiments of struts disclosed herein that incorporates micro-blasting techniques.

Steps that may be included in one embodiment of a manufacturing process 900 that uses micro-blasting are shown schematically in FIG. 9. At 910, the frame may be laser cut from a tube, such as a stainless steel, nitinol, or similar tube, resulting in a plurality of struts, such as strut 912, having the generally trapezoidal cross section, with corners 913, 915. At 920, corners 913, 915 of the strut may be chamfered using lasers, grinding wheels, or the like to provide an initial modification of corner radii for the strut 912. At 930, a mask 932 may be applied to the strut 912, wherein the mask may be a preconfigured chamber that covers one or more sides or parts of sides of the strut but leaves one or more corners exposed to the corner rounding processing method. Alternatively, the mask may consist of a hardened, removable substance that is coated over the strut. At 935, the strut 912 is micro-blasted, smoothing edges 913, 915 (from steps 910, 920) to become rounded exposed portions 936, 937 of the strut 912. The resulting corner rounded strut 912 is shown as the final stage 940 in FIG. 10. While micro-blasting is described herein, it is appreciated that alternate methods, including electropolishing, may be substituted herein by those of skill in the art without affecting the scope of this disclosure.

Accordingly, an implant comprising a plurality of interconnected struts has been shown and described, wherein at least a portion of the struts are manufactured to reduce stresses and strains resulting from component interaction during chronic use.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. An implant for reshaping a valve annulus, the implant comprising:
a tubular frame comprising at least one elongate strut having a proximal portion, a distal portion, and a plurality of sides;
wherein:
adjacent sides of the at least one elongate strut extend along each other along a respective strut corner; and
at least one strut corner of at least one elongate strut is rounded along the proximal portion thereof relative to the distal portion thereof.

2. The implant of claim 1, wherein at least two strut corners of the at least one elongate strut are rounded along a the proximal portion thereof relative to the distal portion thereof.

3. The implant of claim 2, wherein the at least two rounded strut corners have different corner radii.

4. The implant of claim 1, wherein the at least one elongate strut is rounded to have one of a semicircular, ovoid, or circular cross section along the proximal portion thereof.

5. The implant of claim 1, wherein the at least one elongate strut includes a pair of adjacent elongate struts each having a strut corner rounded along the proximal portion thereof relative to the distal portion thereof, the rounded strut corners of the pair of adjacent elongate struts being oriented towards each other.

6. The implant of claim 1, wherein the at least one rounded strut corner comprises a corner radius of between 0.001" and 0.1".

7. The implant of claim 1, wherein the at least one elongate strut includes a pair of adjacent elongate struts joined along a proximal apex, the frame further including a collar disposed at least partially around a proximal apex of the pair of adjacent elongate struts, the collar comprising a proximal end and a distal end, and disposed to axially translate along the pair of adjacent elongate struts to a distal extent of travel, wherein each elongate strut of the pair of adjacent elongate struts includes at least one rounded portion disposed at least partially within the distal end of the collar at the distal extent of travel of the collar.

8. The implant of claim 7, further comprising:
a shaft carried by the proximal apex of the pair of adjacent elongate struts and having an outer thread;
wherein:
the shaft is configured to rotate about a rotation axis;
the collar has an inner thread engaged with the outer thread of the shaft; and
rotation of the shaft about the rotation axis causes the collar to axially translate along the pair of adjacent elongate struts to change an angle between the pair of adjacent elongate struts.

9. The implant of claim 8, wherein the pair of elongate struts is one of a plurality of elongate struts of the tubular frame, and wherein the plurality of elongate struts are joined in pairs at their proximal portions to provide a plurality of pairs of adjacent elongate struts, and wherein the plurality of pairs of adjacent elongate struts are joined at their distal portions to provide a plurality of distal apices, and the implant includes a plurality of anchors translatably supported by the plurality of distal apices.

10. An implant comprising:
a frame comprising a plurality of elongate struts, at least two elongate struts each having a proximal portion, a distal portion, and a plurality of sides;
a plurality of anchors; and
at least one collar;
wherein:
adjacent sides of each of the at least two elongate struts extend along each other along a respective strut corner;
the proximal portion of each of the at least two elongate struts includes a rounded portion extending partially therealong and including a rounded strut corner;
the proximal portions of the each of the at least two elongate struts are joined to form a pair of adjacent elongate struts having a proximal apex;
wherein:
the pair of adjacent elongate struts is joined to an adjacent pair of elongate struts at a distal apex, the distal apex configured to support one of the plurality of anchors;
the rounded portion of at least one of the at least two elongate struts has one of a semicircular, ovoid, or circular cross section; and
the at least one collar is slidably disposed along and at least partially around the proximal apex of the pair of adjacent elongate struts, the collar comprising a proximal end and a distal end, the collar being shaped and configured to axially translate along the pair of adjacent elongate struts to a distal extent of travel, wherein the rounded portions of the elongate struts of the pair of adjacent elongate struts are at least partially within the distal end of the collar in the distal extent of travel of the collar.

11. The implant of claim 10, wherein the rounded portion of the other of the at least two elongate struts includes at least two corners rounded to a common corner radius or a different corner radii.

12. The implant of claim 11, wherein a portion of the rounded portion of the other of the at least two elongate struts is oriented towards the at least one of the at least two of the elongate struts which has the semicircular, ovoid, or circular cross section.

13. The implant of claim 10, wherein the rounded portion of at least one of the at least two elongate struts comprises a circular cross section with a radius between 0.001" and 0.1".

14. The implant of claim 10, wherein the at least two elongate struts are rounded with different degrees of rounding.

15. A method of manufacturing an implant comprising a tubular frame comprising at least one elongate strut having a proximal portion, a distal portion, and a plurality of sides, adjacent sides of the at least one elongate strut extend along a respective strut corner, wherein the proximal portion of the at least one elongate strut includes a rounded portion extending partially along the proximal portion of the at least one elongate strut and including a rounded strut corner, the method comprising:
cutting the at least one elongate strut from a metal tube; and
performing a rounding process on only the proximal portion relative to the distal portion of the at least one elongate strut to form the rounded strut corner, the rounding process including cutting, grinding, milling, electropolishing, micro-blasting, etching, or a combination thereof.

16. The method of claim 15, including everting the tubular frame or masking the tubular frame, or both.

17. The method of claim 14, wherein the rounded strut corner is associated with a first corner of the at least one elongate strut and comprises a first corner radius, and the rounding process includes performing the rounding process on a second corner of the at least one elongate strut to provide a second rounded corner having a second corner radius that is common or different from the first corner radius.

18. The method of claim 17, wherein performing the rounding process on the second corner occurs simultaneously with performing the rounding process on the first corner.

19. The method of claim 15, wherein the at least one elongate strut is one of a plurality of elongate struts of the tubular frame, the method further comprising performing the rounding process on each of the plurality of elongate struts of the tubular frame, wherein at least two rounded portions of at least two different elongate struts are similar or different.

* * * * *